(12) United States Patent
Lindemann et al.

(10) Patent No.: US 8,267,978 B2
(45) Date of Patent: Sep. 18, 2012

(54) HYBRID BONE FIXATION APPARATUS

(75) Inventors: Gary Lindemann, Collierville, TN (US); Stephen M. Papadopoulos, Paradise Valley, AZ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1442 days.

(21) Appl. No.: 11/520,946

(22) Filed: Sep. 14, 2006

(65) Prior Publication Data

US 2008/0086129 A1    Apr. 10, 2008

(51) Int. Cl.
*A61B 17/86* (2006.01)

(52) U.S. Cl. ........................................ 606/305; 606/267

(58) Field of Classification Search .................. 606/267, 606/278, 287, 288, 300–330; 411/337–377
See application file for complete search history.

(56) References Cited

U.S. PATENT DOCUMENTS

| | | | | |
|---|---|---|---|---|
| 5,807,051 A * | 9/1998 | Heminger | | 411/82 |
| 6,117,173 A * | 9/2000 | Taddia et al. | | 623/16.11 |
| 6,302,630 B1 * | 10/2001 | Grant | | 411/372.6 |
| 6,575,975 B2 * | 6/2003 | Brace et al. | | 606/86 B |
| 7,235,079 B2 * | 6/2007 | Jensen et al. | | 606/151 |
| 2002/0133158 A1 | 9/2002 | Saint Martin | | |
| 2004/0127904 A1* | 7/2004 | Konieczynski et al. | | 606/70 |
| 2004/0243129 A1 | 12/2004 | Moumene et al. | | |
| 2005/0187550 A1 | 8/2005 | Grusin | | |
| 2005/0187555 A1 | 8/2005 | Biedermann et al. | | |
| 2005/0203516 A1 | 9/2005 | Biedermann et al. | | |
| 2005/0203517 A1 | 9/2005 | Jahng et al. | | |
| 2005/0203519 A1 | 9/2005 | Harms et al. | | |
| 2005/0228388 A1 | 10/2005 | Brodke et al. | | |
| 2006/0235410 A1* | 10/2006 | Ralph et al. | | 606/72 |

FOREIGN PATENT DOCUMENTS

| | | |
|---|---|---|
| DE | 44 43 051 | 10/1996 |
| DE | 100 65 799 | 4/2002 |
| FR | 2 899 787 | 10/2007 |
| GB | 2 294 399 | 5/1998 |

* cited by examiner

*Primary Examiner* — Eduardo C Robert
*Assistant Examiner* — Steven Cotroneo

(57) ABSTRACT

An orthopedic bone fixation device including an anchor member having a cavity and an insert member. The anchor member retains the insert member at least partially or entirely in the cavity. The insert member has an insert aperture for accommodating part of a screwdriver or other device.

15 Claims, 5 Drawing Sheets

HYBRID BONE FIXATION APPARATUS

The present disclosure relates to devices and implants used in osteosynthesis and other orthopedic surgical procedures. Specifically, the present disclosure includes a bone fixation device having an anchor member and an insert member.

Several techniques and systems have been developed for correcting and stabilizing damage or malformation of bones, especially the spine. Screws, hooks, clamps and other types of anchors or other devices have been proposed for orthopedic correction and/or stabilization. Several materials have been used to manufacture such devices. For example, a screw made of polyether ether ketone (PEEK) may generally have a low shear strength and a low torsion strength when compared to metal screws. Other types of screws have been made out of titanium or stainless steel. However, stainless steel or titanium screws are not radiolucent, and they may be prone to x-ray or MRI artifacts, especially near the tip of the screw, or in regions where a surgeon looks to extract information about the implant device and/or the tissues, e.g. in the area of the spinal column and vertebral arteries.

DESCRIPTION OF THE ILLUSTRATED EMBODIMENTS

Figure 1:
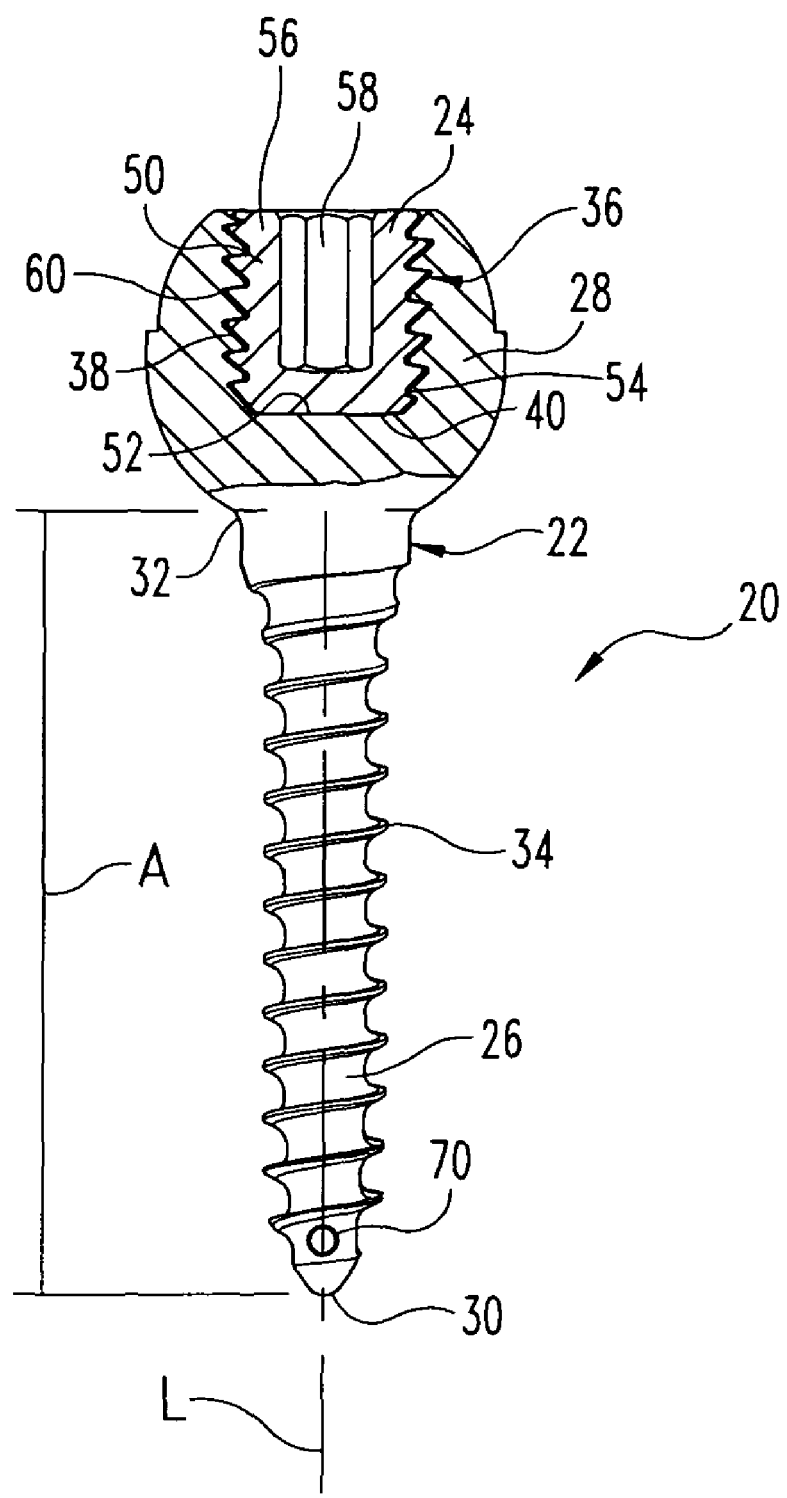
FIG. 1 is a side elevational view with a partial cross sectional view of one embodiment of a bone fixation device.

For the purposes of promoting an understanding of the principles of the disclosure, reference will now be made to the embodiments illustrated in the drawings and specific language will be used to describe the same. It will nevertheless be understood that no limitation of the scope of the claims is thereby intended, such alterations and further modifications in the illustrated devices, and such further applications of the principles of the disclosure as illustrated therein, being contemplated as would normally occur to one skilled in the art to which the disclosure relates.

Referring generally to the figures, there are shown embodiments of a bone fixation device 20. In the illustrated embodiment, device 20 includes an anchor member 22 and an insert member 24. Device 20 can be connected to bone, such as a vertebra, or other tissue, and can be used in connection with orthopedic plates, connectors, rods or other types of instrumentation or implants.

In the illustrated embodiment shown in FIG. 1, anchor member 22 includes a shaft portion 26 and a head portion 28. Shaft portion 26 has a first end 30 and a second end 32 with a length A spanning between the ends. Shaft portion 26 includes a longitudinal axis L along the length. As shown, first end 30 can be a tapered end, or in other embodiments first end 30 could be flat or otherwise configured. In one embodiment, threads 34 form a helical pattern around shaft portion 26 substantially from first end 30 towards second end 32, and may extend along substantially the entire length A of shaft portion 26. It will be seen that other embodiments of device 20 could have threads 34 along a part of length A of shaft portion 26. Further, threads 34 in the illustrated embodiment have a single lead, but it is understood that multiple-lead threads (e.g. having two leads) could be used on shaft 26. Threads 34 can be of a standard cancellous formation or of any shape or configuration that enables engagement with human tissue or bone.

Head portion 28 is substantially spherical in shape in the illustrated embodiment. In other embodiments, head portion 28 may have another shape such as a cube or a trapezoid. Head portion 28 defines a cavity 36 with one or more cavity walls 38 and a lower surface or cavity base 40. The illustrated embodiment of cavity 36 is substantially cylindrical, and therefore a single continuous cylindrical wall 38 is defined. If cavity 36 is rectangular, triangular or otherwise polygonal, then a number of walls 38 may surround cavity 36. Similarly, if a U-shaped channel were to be included through head portion 28 and cavity 36, then such channel can create two or more sections or walls 38. In the embodiment shown in FIG. 1, cavity base 40 is substantially perpendicular to axis L, and cavity wall(s) 38 are substantially parallel to axis L. Cavity wall(s) 38 and base 40 can also be slanted or taper, e.g. form an oblique angle, with respect to axis L cavity wall 38 and/or each other.

Cavity 36 is shaped and sized to be compatible with insert member 24. In the illustrated embodiment, insert member 24 is fully inserted in cavity 36, although it is possible to have insert member 24 only partially inserted in cavity 36. For example, in one embodiment, cavity wall 38 and insert member 24 are each threaded such that insert member 24 can be twisted or rotated into cavity 36 and thread with cavity wall 38. Cavity 36 may be beveled in some embodiments, such that wall(s) 38 open out via a substantially conical surface 42 (FIG. 3), so that surface 42 slants with respect to wall(s) 38. As described in more detail below, insert member 24 can include a corresponding flange portion to contact surface 42.

Figure 2:
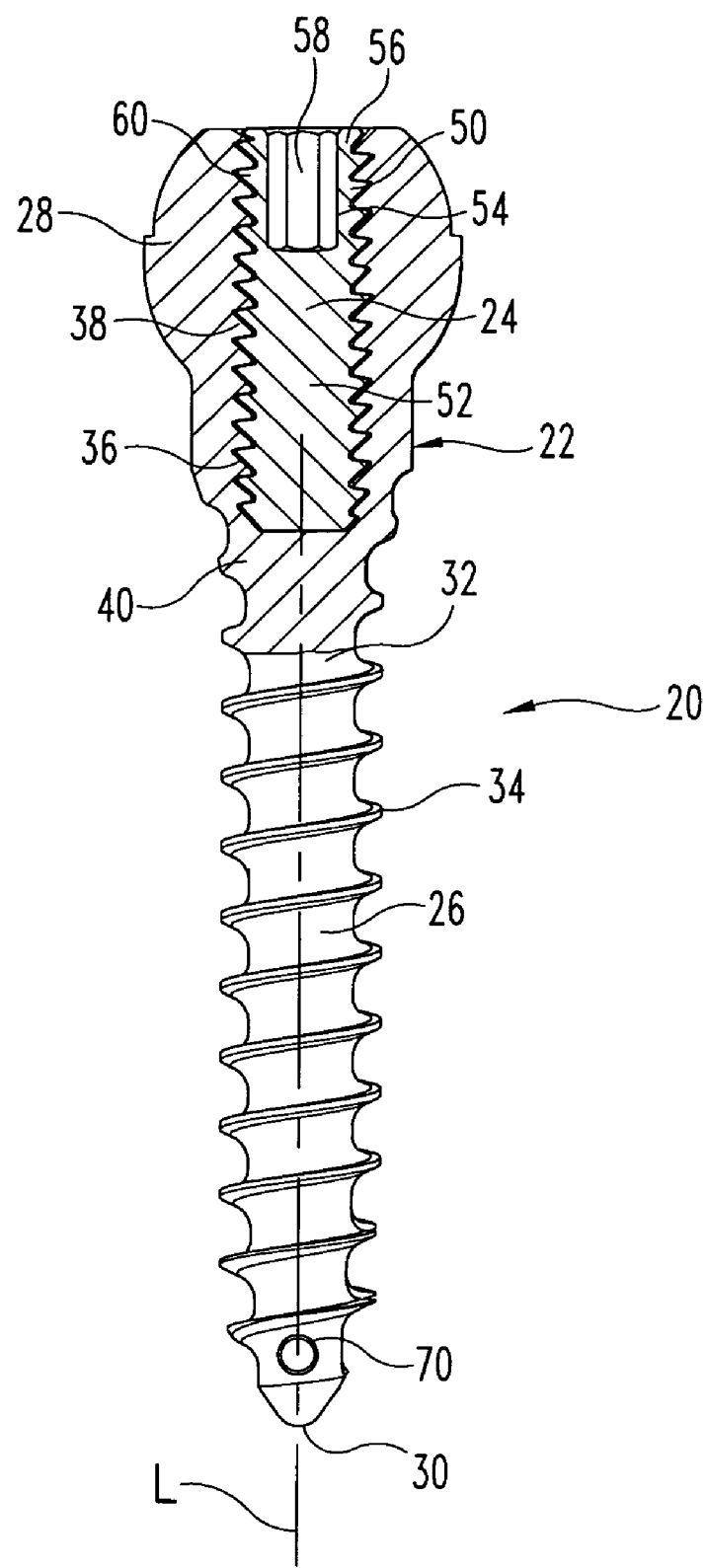
FIG. 2 is a side elevational view with a partial cross sectional view of another embodiment of a bone fixation device.

Cavity 36 may have a variety of lengths in different embodiments. For example, FIG. 1 shows cavity 36, with its wall(s) 38 and base 40, contained within head portion 28. Alternatively, as shown in FIG. 2, cavity 36 and its wall(s) 38 and base 40 may extend through head portion 28 along axis L into shaft portion 26, such that base 40 is positioned in shaft portion 26.

Anchor member 22 may be made of any biocompatible material. Biocompatible metals include titanium, stainless steel, titanium alloys, nickel-titanium alloys, nitinol, and chrome alloy, to name a few. Biocompatible plastics include polyurethane, polyester, polyether, polyalkene, polyethylene, polyamide, polyvinyl fluoride, polyether ether ketone (PEEK), or polytetrafluoroethylene (PTFE). In the illustrated embodiment, shaft portion 26 and head portion 28 are made of the same material, and in particular embodiments shaft portion 26 is made of PEEK or another radiolucent body-compatible material. It has been found that a shaft portion 26 made of radiolucent material minimizes x-ray and MRI artifacts, such as at first end 30 near an area where the surgeon can extract valuable information concerning the spinal column and vertebral arteries when anchor member 22 is inserted in a vertebra. It will be seen that shaft portion 26 and head portion 28 could be made of different materials. For example, shaft portion 26 may be made of a biocompatible metal and head portion 28 may be made of a biocompatible plastic.

In some embodiments, a radiopaque marker 70 can be placed on or in a part of anchor member 22. For example, radiopaque marker 70 in the form of a dot, cylinder or sphere of metal or other material can be positioned in or adjacent first end 30 of anchor member 22. In other embodiments, radiopaque marker 70 can be positioned elsewhere on shaft portion 26 or head portion 28. Marker 70 placed on or within shaft portion 26, for example, which is made of a radiolucent material such as PEEK, provides a point or location on shaft 26 that clearly registers on an x-ray picture, MRI or CT scan, or other forms of imaging. Even so, the radiolucent quality of a PEEK shaft portion 26 reduces or eliminates artifacts in x-ray, MRI or other imaging procedures. The surgeon or other medical professionals can identify the location of anchor member 22 via radiopaque marker 70, while lessening or avoiding observation mistakes due to such artifacts.

Anchor member 22 may also be coated with a bioactive material such as, for example, growth factors for bone ingrowth and bone attachment, or for soft tissue ingrowth. Examples of growth factors may include insulin-like growth factor, basic fibroblast growth factor, transforming growth factor, platelet-derived growth factor, bone-derived growth factors, arginine, bone morphogenetic protein, LIM mineralization protein, and combinations thereof.

Insert member 24, in the illustrated embodiment, is substantially cylindrical and includes an insert wall 50 and an insert base 52 as shown in FIGS. 1 and 2. Insert wall 50 has a first end 54 and an opposite second end 56. As noted above, insert member 24 is generally configured to fit within cavity 36, and may have a shape and size similar or substantially identical to the shape or size of cavity 36. Thus, where cavity 36 is polygonal, insert member 24 may be of substantially the same polygonal shape. Further, where head portion 28 and cavity 36 are substantially U-shaped, insert member 24 may also be U-shaped (having multiple wall portions 50) so that a channel extends through head portion 28 and insert member 24. In other embodiments, insert member 24 may have a shape different from that of cavity 36. As one example, if cavity 36 is substantially cylindrical, insert member 24 may be square, with a diagonal length at least slightly greater than the diameter of cavity 36, so that corners of such an insert member will firmly engage wall(s) 38 of cavity 36. Where insert member 24 and cavity 36 are each substantially cylindrical, the diameter of insert member 24, or some part of it, may be slightly larger than the diameter of cavity 36.

Insert member 24 further includes an insert aperture 58 in the illustrated embodiment. Wall(s) 50 may have a substantially constant thickness measured between aperture 58 and the outer surface of insert member 24, and insert base 52 may have a similar thickness to that of wall(s) 50, as measured between the bottom of aperture 58 and the outer surface of insert member 24. In other embodiments, base 52 may be a different thickness than wall(s) 50. For example, as indicated in FIG. 2, base 52 is substantially thicker than wall 50.

Aperture 58 is sized and shaped to receive a screwdriver or other tool or instrument used for gripping, holding or applying a rotational force to bone fixation device 20, as described in more detail below. In the illustrated embodiment, aperture 58 is substantially hexagonal. In other embodiments, aperture 58 may be hexalobed, rectangular, star-shaped, one or more slits, or other shapes that are adapted to accept turning or gripping tools.

Figure 3:
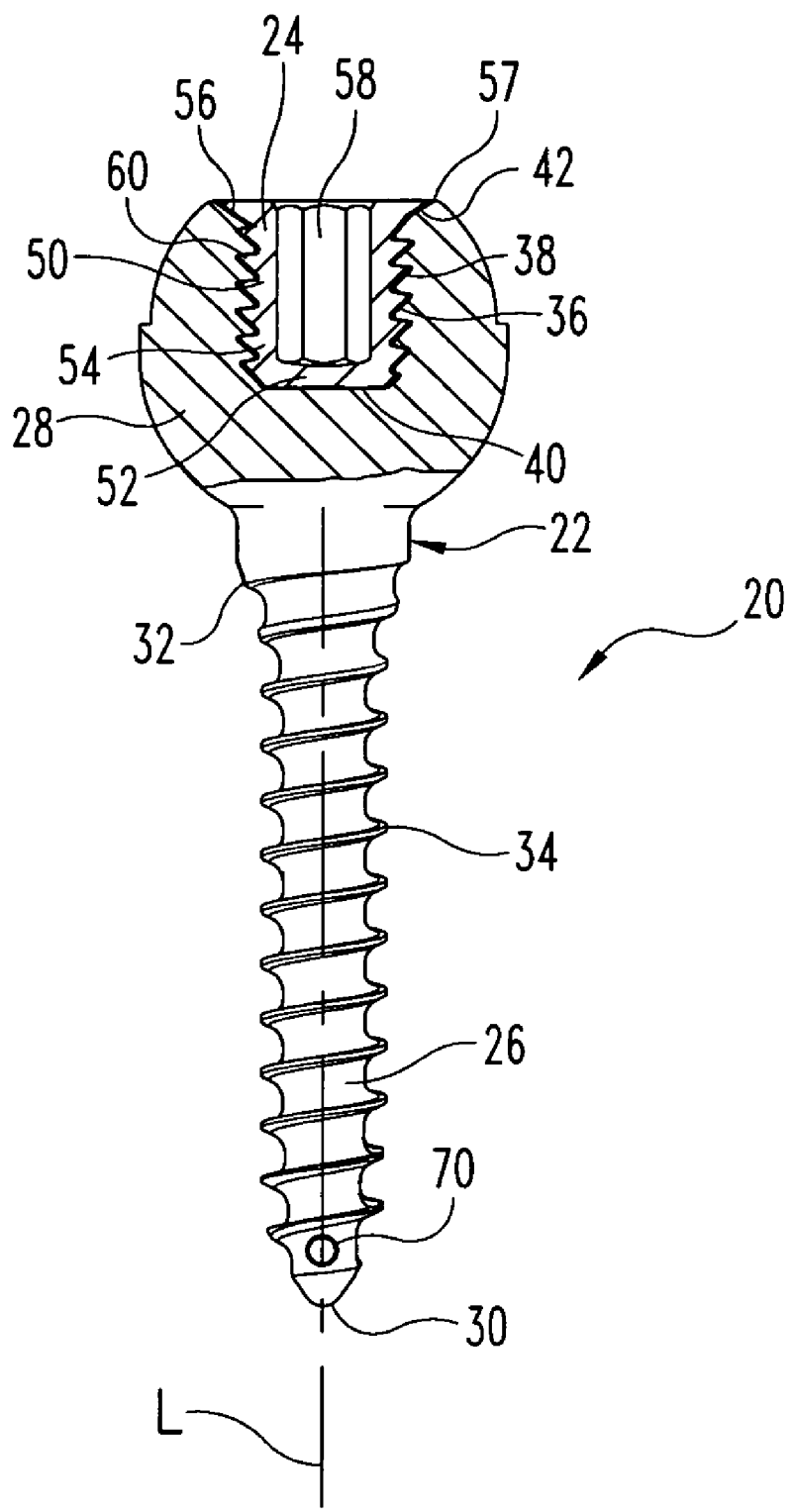
FIG. 3 is a side elevational view with a partial cross sectional view of another embodiment of a bone fixation device.

In a particular embodiment, illustrated in FIG. 3, insert member 24 includes a flange 57 adjacent second end 56, which contacts surface 42 of head portion 28. Flange 57 may be configured substantially similarly to surface 42, and thus in one embodiment has a substantially conical underside that mates with the illustrated embodiment of surface 42.

Insert member 24 may further include one or more protrusions 60 extending from wall 50. As indicated in the figures, protrusion(s) 60 may be single- or multiple-lead threads extending along the length of wall 50 substantially from first end 54 to second end 56. The thread protrusion(s) 60 may be helically oriented in the same manner as threads 34 of anchor member 22, e.g. right-handed threads in a particular embodiment. In that configuration, insert member 24 may be turned and threaded into anchor member 22 until insert member 24 seats within cavity 36, and then further turning force exerted on insert member 24 operates to thread anchor member 22 into tissue, as further described below. In other embodiments, protrusion(s) 60 in the form of threads or other forms may extend along only a part of wall 50. In addition to right- or left-handed threads, protrusion(s) 60 can be one or more pyramids, bumps, rectangles, barbs, or other shapes that generate a friction or interference fit, or pierce wall 38 of head portion 28. Thus, protrusion(s) 60 engage and/or penetrate cavity wall 38 when insert member 24 is inserted into anchor member 22, as for example when base 52 of insert member 24 contacts cavity base 40 of head 28.

Insert member 24 may be made of any sturdy biocompatible material, particularly metals. For example, insert member 24 may be made of biocompatible metals such as titanium, stainless steel, titanium alloys, nickel-titanium alloys, nitinol, chrome alloy, to name a few.

Insert member 24 may be inserted into or otherwise attached to anchor member 22 by various methods. In one embodiment, anchor member 22 can be overmolded or shaped around insert member 24, particularly where anchor member 22 is made of PEEK or another biocompatible plastic material that is easily made flowable and formed in a mold. In one form, while the plastic material is within a mold and soft, insert member 24 can be inserted into the soft head portion 28 of anchor member 22. That insertion forms cavity 36 around insert member 24, and if insert member 24 includes protrusion(s) 60, the plastic material can flow around or otherwise accommodate such protrusion(s) 60. The plastic material is then allowed to harden or otherwise cured around insert member 24. Generally, such a hardening or curing process will result in at least a slight contraction of the plastic material. With such contraction, and with the interdigitation or extension of any protrusion(s) 60 into the plastic material, insert member 24 is held within anchor member 22. In another form, insert member 24 can be positioned in a mold, and then flowable biocompatible plastic material is injected into the mold or otherwise placed around insert member 24. As described above, the plastic material will form around insert member 24, creating cavity 36 and a close fit around any protrusion(s) 60 on insert member 24. After curing or hardening, insert wall 50 and insert base 52 remain attached to and in contact with cavity wall 38 and cavity base 40, respectively.

In another embodiment, insert member 24 can be ultrasonically inserted into cavity 36 of anchor member 22. In such a method, anchor member 22 can be preformed of PEEK or another appropriate biocompatible plastic to include cavity 36 of a size approximately the same as or slightly smaller than the size of insert member 24. Ultrasonic energy, or other suitable energy for heating a portion of anchor member 22, is applied to head portion 28, particularly in the area of cavity 36, to soften the material adjacent cavity 36. Insert member 24 can be inserted into cavity 36 such that insert wall 50 contacts cavity wall 38, insert base 52 contacts cavity base 40, and plurality of protrusions 60 engage cavity wall 38. Hardening or other curing of the softened part(s) of head portion 28, as discussed above, provide a tight fit between anchor member 22 and insert member 24 and its protrusion(s) 60, if any.

Where protrusion(s) 60 are threads, insert member 24 can be turned into cavity 36 of anchor member 22 so as to be threadably inserted. Anchor member 22 may be formed with or without female threads in wall(s) 50 around cavity 36. If such female threads are provided, either by a molding process or by tapping with a tap instrument, then they may be of substantially the same configuration as thread protrusion(s) 60. If such female threads are not provided, and the diameter of cavity 36 is at least slightly smaller than a crest diameter of thread protrusion(s) 60, then thread protrusion(s) 60 can cut a female thread path in wall(s) 38 around cavity 36. Cutting of such a path is somewhat easier when the PEEK or other material adjacent cavity 36 is somewhat soft or pliable, although many sturdy biocompatible plastics may allow such cutting by a metal thread without substantial risk of cracking.

Figure 4:
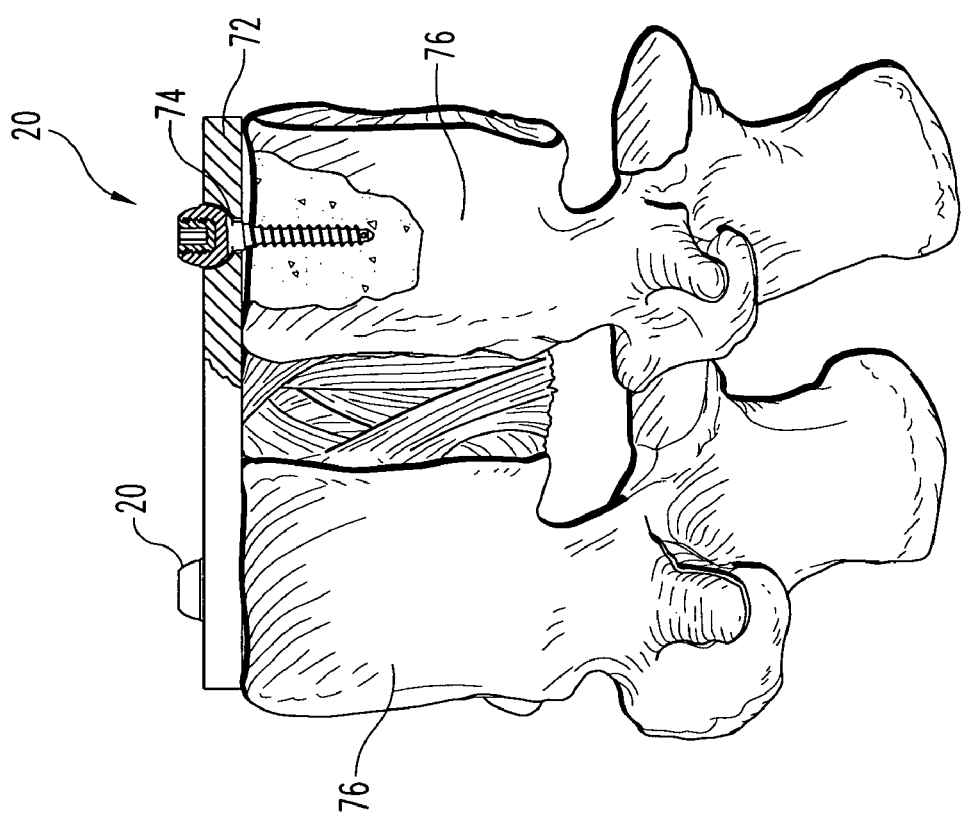
FIG. 4 is a partial cross-sectional view of an embodiment of a bone fixation device fixing an embodiment of an elongated member to a portion of the spine.

Once device 20 has been manufactured or assembled, such as by one of the methods discussed above, it can be used in orthopedic surgery. As noted above, device 20 can be used with a variety of orthopedic implants, such as vertebral plates, connectors and other apparatus. With the illustrated embodiments, in which anchoring member 22 is a screw, the threaded shaft 26 can be rotated and threadedly inserted into a bone or other tissue. For example, referring generally to FIG. 4, a plate member 72 having a hole 74 through it can be attached to a vertebra 76 or other tissue by extending device 20 through the hole in the plate and into the tissue, tightening head portion 28 against the plate member and fixing the plate member to the bone.

Figure 5:
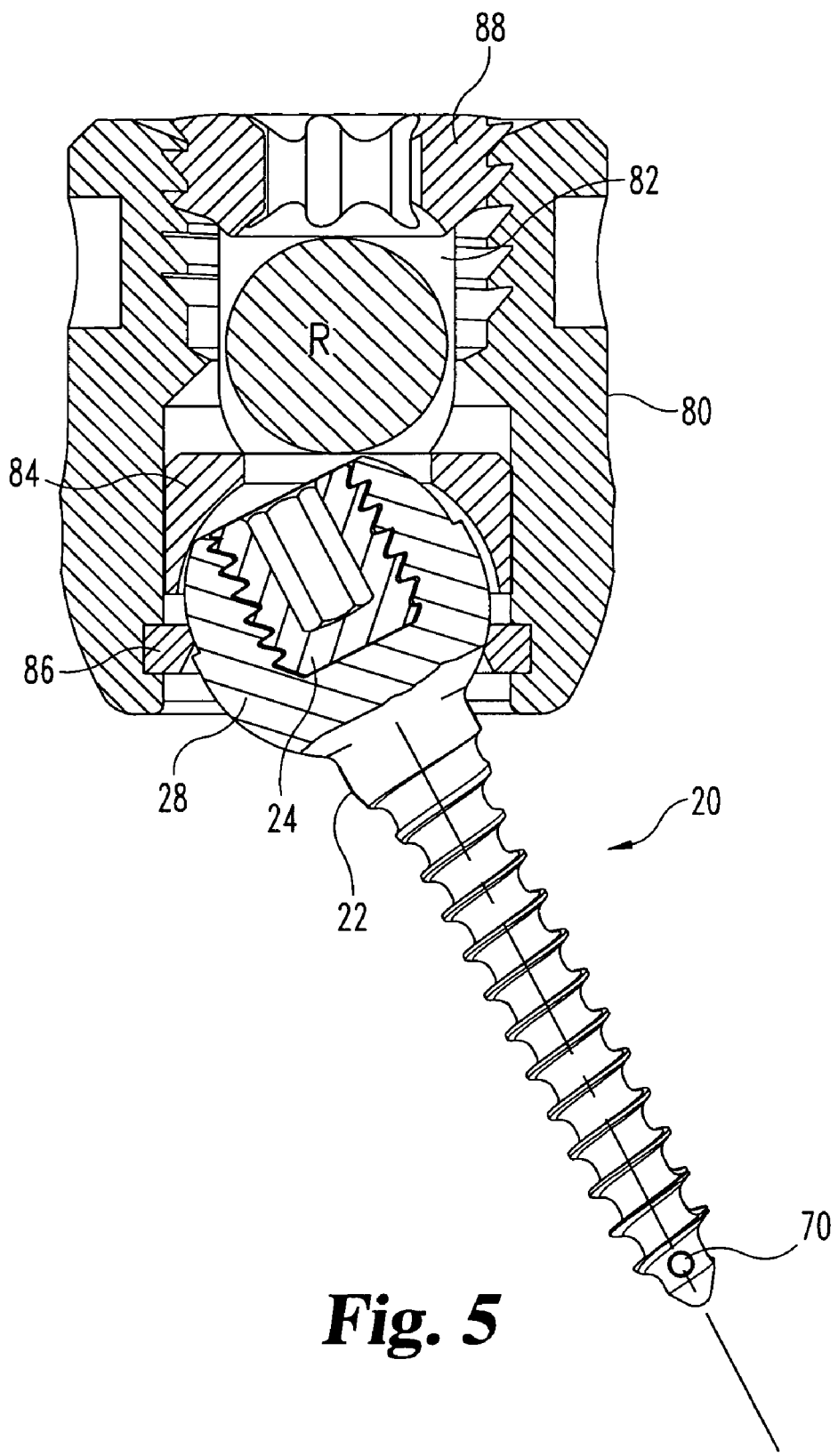
FIG. 5 is a partial cross-sectional view of an embodiment of a multi-axial bone anchor using an embodiment of a bone fixation device disclosed herein.

Device 20 can also be used as a part of a larger anchor construct. For example, device 20 could be used as the anchor portion of a multi-axial bone anchor. Referring generally to FIG. 5, in certain types of multi-axial bone screws, a receiver member 80 having a U-shaped channel 82 is provided, through which an anchor member such as the illustrated embodiment of device 20 can extend. Such a multi-axial anchor construct may also include one or more of a crown member 84, a retaining ring 86, and a locking member 88, and may be connected to an elongated member such as rod R. Further disclosure of embodiments of a multi-axial screw are shown in U.S. Pat. No. 6,280,442, which is incorporated herein by reference.

Other embodiments of bone fixation device 20 are contemplated as being within the scope of the present disclosure. For example, anchor member 22 could include a curved blade of a bone-engaging hook rather than a threaded shaft of a screw. Bolts, clamps and other types of implants can include aspects of the present disclosure.

A metal insert member 24 provides additional strength to a PEEK or other plastic anchor member 22, particularly in the head area, which is under the most strain as device 20 is rotated by a screwdriver or other tool to insert it into a bone. A metal screwdriver acts directly on a metal insert member, and not on the potentially softer or more malleable plastic, thus limiting or preventing damage from a screwdriver to head portion 28 of anchor member 22. Thus, the biocompatible PEEK (or other plastic of the anchor member 22) contacts the bone and/or other tissue, with a reduction in tissue trauma and potential for tissue ingrowth associated with that material, while the insertion tool acts on the stronger metal insert member 24. A metal insert member 24 in an anchor member 22 of PEEK or other plastic provides a smaller radiopaque marker within head portion 28, rather than an entire head or an entire anchor made of metal. In embodiments having a radiopaque marker in shaft portion 26, device 20 accordingly affords two discrete markers for imaging while minimizing imaging artifacts or other errors. Insert member 24 can also be colored differently than anchor member 22.

While the disclosure has been illustrated and described in detail in the drawings and foregoing description, the same is to be considered as illustrative and not restrictive in character, it being understood that only the preferred embodiment has been shown and described and that all changes and modifications that come within the spirit of the disclosure are desired to be protected.

What is claimed is:

1. A fixation device for orthopedic medical use comprising:
    an anchor member having an anchor portion for engaging a bone and a head portion, said head portion made of a polymer material and defining a cavity defining at least one cavity wall and a cavity base defining a bottom surface of said cavity, said cavity wall and said cavity base contained within said head portion of said anchor member; and
    an insert member made of a metallic material and having an insert wall and an insert base, said insert wall having at least one external protrusion, said insert member defining an aperture sized to receive a medical instrument,
    wherein said insert is positioned within said cavity in said head portion of said anchor member with said insert base in contact with said bottom surface of said cavity base.

2. The device of claim 1, wherein:
    said metallic material is titanium.

3. The device of claim 1, wherein said polymer material is polyether ether ketone.

4. The device of claim 1, wherein said anchor portion is made of said polymer material; and
    further comprising a radiopaque marker in or on said anchor portion.

5. The device of claim 1, wherein:
    said at least one protrusion includes a thread.

6. The device of claim 1, wherein:
    said insert wall has a first end and a second end, said first end includes an insert flange; and
    said insert member is substantially flush with an end of said anchor member and is substantially contained in said head portion of said anchor member.

7. An orthopedic medical apparatus comprising:
    an anchor member made of polyether ether ketone having a shaft portion and a head portion, said shaft portion having a longitudinal axis, said head portion having a cavity along said longitudinal axis, said cavity defining at least one wall and a cavity base defining a bottom surface of said cavity, said cavity substantially contained within said head portion of said anchor member;
    an insert member made of metal defining an internal aperture, said insert sized to substantially fit within said cavity and substantially contained in said head portion of said anchor member; and
    said insert member having at least one protrusion penetrating into said wall; and
    said insert member includes an insert wall having a first end and a second end, said first end including a flange;
    said flange is substantially flush with an end of said anchor member; and
    said second end of said insert member contacts said cavity base.

8. The apparatus of claim 7, further comprising a radiopaque marker in or on said shaft portion.

9. The apparatus of claim 7, wherein said aperture has a hexagonal cross sectional shape.

10. The apparatus of claim 7, wherein said shaft portion includes threads for engaging a bone.

11. An orthopedic medical apparatus comprising:
    an anchor member made of polyether ether ketone having a shaft portion and a head portion, said shaft portion having a longitudinal axis, said shaft portion being threaded to define an externally threaded portion extending along a length of said shaft portion, said head portion having a cavity extending along said longitudinal axis and defining a cavity wall and a cavity base defining a bottom surface, said cavity extending at least partially through said head portion of said anchor member but not into said externally threaded portion of said anchor member;

an insert member made of a metallic material having an insert wall and an insert base and defining an aperture sized to receive a tool, said insert sized to substantially fit in said cavity wherein said insert base contacts said bottom surface of said cavity base and said insert wall contacts said cavity wall; and said insert member having at least one protrusion that penetrates into said anchor member.

12. The apparatus of claim 11, wherein said insert member is substantially contained in said head portion of said anchor member.

13. The apparatus of claim 11, wherein:
said at least one protrusion is a thread.

14. The apparatus of claim 11, wherein:
said insert member includes a first end and a second end; and
said insert includes an insert flange at said first end.

15. The apparatus of claim 14, wherein said insert flange is slanted with respect to said insert wall.

* * * * *